(12) United States Patent
Konawa

(10) Patent No.: US 11,116,676 B2
(45) Date of Patent: Sep. 14, 2021

(54) DISPOSABLE DIAPER

(71) Applicant: DAIO PAPER CORPORATION, Ehime (JP)

(72) Inventor: Satoko Konawa, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 898 days.

(21) Appl. No.: 15/514,411

(22) PCT Filed: Sep. 25, 2015

(86) PCT No.: PCT/JP2015/077201
§ 371 (c)(1),
(2) Date: Mar. 24, 2017

(87) PCT Pub. No.: WO2016/047787
PCT Pub. Date: Mar. 31, 2016

(65) Prior Publication Data
US 2017/0296400 A1 Oct. 19, 2017

(30) Foreign Application Priority Data
Sep. 26, 2014 (JP) .............................. JP2014-196377

(51) Int. Cl.
*A61F 13/49* (2006.01)
*A61F 13/496* (2006.01)
*A61F 13/53* (2006.01)

(52) U.S. Cl.
CPC ........ *A61F 13/49012* (2013.01); *A61F 13/49* (2013.01); *A61F 13/496* (2013.01); *A61F 13/49019* (2013.01); *A61F 13/53* (2013.01)

(58) Field of Classification Search
CPC .......... A61F 13/49012; A61F 13/49019; A61F 13/49; A61F 13/496; A61F 13/53
See application file for complete search history.

(56) References Cited

U.S. PATENT DOCUMENTS 5,484,430 A * 1/1996 Osborn, III ........... A61F 13/472
604/385.21
5,514,104 A * 5/1996 Cole ..................... A61F 5/4401
604/358

(Continued)

FOREIGN PATENT DOCUMENTS

CN 102958483 3/2013
EP 2589360 A1 5/2013

(Continued)

OTHER PUBLICATIONS

English translation of JP-4439425.*

*Primary Examiner* — Tatyana Zalukaeva
*Assistant Examiner* — Jessica R Arble
(74) *Attorney, Agent, or Firm* — Muncy, Geissler, Olds & Lowe, P.C.

(57) ABSTRACT

The present invention is intended to make the deformation of the absorber at the crotch portion less prone to influence the waist side of the absorber and allow the waist side of the absorber to be easily rounded along the surface of the wearer's body. The foregoing issue is solved by a disposable diaper including an absorber in a crotch portion, a ventral-side portion, and a dorsal-side portion, wherein the absorber is divided in a front-back direction by width-direction slits continuing in the width direction provided on both front and back sides of the crotch portion, and concave portions recessed toward the waist side are formed in width-direction centers of waist-side edges of the width-direction slits.

8 Claims, 14 Drawing Sheets

(56) References Cited

U.S. PATENT DOCUMENTS

| | | | |
|---|---|---|---|
| 6,293,931 B1 * | 9/2001 | Romare | A61F 13/47218 604/379 |
| 6,503,233 B1 * | 1/2003 | Chen | A61F 13/47218 604/378 |
| 2010/0318053 A1 * | 12/2010 | Smet | A61F 13/49017 604/385.23 |
| 2011/0094661 A1 * | 4/2011 | Thorson | A61F 13/15593 156/211 |
| 2013/0060222 A1 * | 3/2013 | Gerstle | A61F 13/15747 604/385.201 |
| 2014/0031783 A1 * | 1/2014 | Arayama | A61F 13/49001 604/385.101 |

FOREIGN PATENT DOCUMENTS

| | | |
|---|---|---|
| JP | H0428363 A | 1/1992 |
| JP | H11332913 A | 12/1999 |
| JP | 2002035029 A | 2/2002 |
| JP | 2002178428 A | 6/2002 |
| JP | 2002273808 A | 9/2002 |
| JP | 2009011377 A | 1/2009 |
| JP | 4439425 B2 * | 3/2010 |
| JP | 2011177309 A | 9/2011 |
| JP | 2011206269 A | 10/2011 |
| JP | 2013192848 A | 9/2013 |
| JP | 2014158962 A | 9/2014 |

* cited by examiner

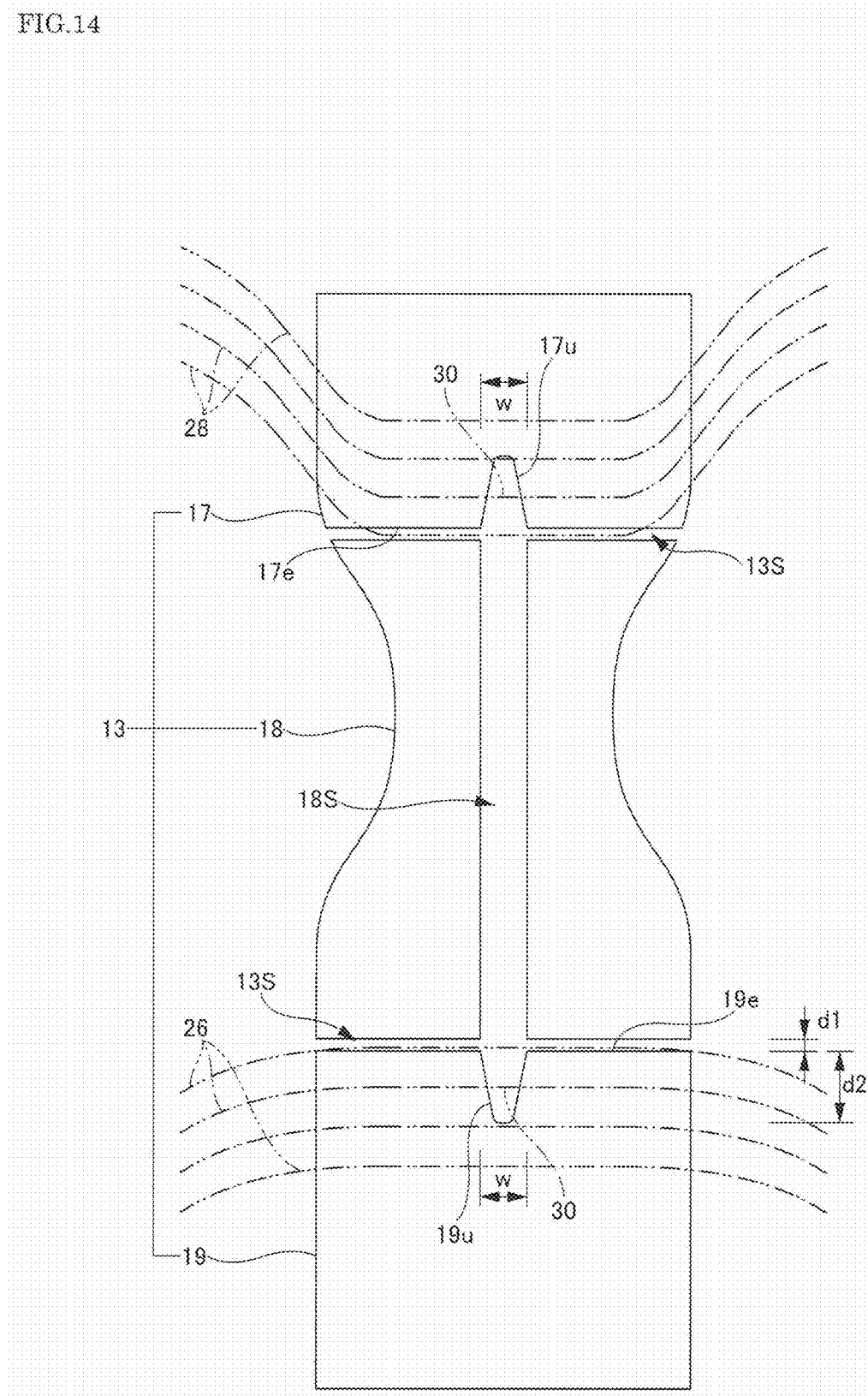

DISPOSABLE DIAPER

TECHNICAL FIELD

The present invention relates to a disposable diaper improved in the fit of an absorber.

BACKGROUND ART

For example, a disposable diaper generally includes an outer body extending from the ventral side through the crotch to the dorsal side of a wearer and an inner body that has an absorber and is fixed to the inner surface of the outer body. The ventral side and the dorsal side of the outer body are joined together at the both side edges to form a waist opening and a pair of right and left leg openings. The inner body includes three-dimensional gathers protruding toward the wearer's body on the both sides of the external surface.

In addition, in the underpants-type disposable diaper, various elastic members such as waist portion elastic members, waist lower portion elastic members, and curved elastic members are fixed in an extended state to the outer body for improvement of a fit to the wearer's body (for example, refer to Patent Documents 1 and 2). The waist portion elastic members are arranged in parallel in a width direction at vertical intervals at the edge of the waist opening. The waist lower portion elastic members are arranged in the width direction at vertical intervals in the region nearer the front-back direction center than the waist portion elastic members. The curved elastic members are curved and extended in at least one of the front panel and the back panel in a pattern ranging from one side seal portion to the crotch portion along one leg opening, crossing over the crotch portion, and reaching the other side seal portion along the other leg opening. In general, these elastic members are finely cut in places overlapping the inner body in the width-direction center to prevent contraction of the inner body.

For a manufactural reason, the inner body is rectangular in planar shape. However, the crotch portion of the absorber is frequently narrowed along the legs for improvement of a fit of the crotch portion.

Besides the underpants-type disposable diapers, there are tape-type disposable diapers in which tapes on the both sides of the dorsal-side portion are fastened to the ventral-side portion and pad-type disposable diapers in which the ventral-side portion and the dorsal-side portion are not connected at the both sides. For these diapers, there have been proposed various techniques for improvement of a fit by elastic members and narrowed shapes of the absorber.

In the disposable diapers, however, the flat-shaped absorber is forcibly deformed along the surface shape of the wearer's body and is pressed against the surface of the wearer's body by the use of tightening force of the elastic members in the respective portions to provide a fit. Accordingly, unnecessary folds are produced in the absorber and gaps are made between the surface of the absorber and the surface of the wearer's body to cause problems of easy leakage and deteriorated wearing feeling.

Various solutions to these problems have been proposed such as making slits or narrower portions in the absorber (for example, refer to Patent Documents 1 and 2) but there is still room for improvement. Specifically, at the time of wearing, the disposable diaper has a crotch portion contracted and deformed under a width-direction contraction force between the legs of the wearer. Accordingly, the contraction is delivered to the waist side, and the waist side of the absorber is unlikely to be rounded along the surface of the wearer's body. There has no technique proposed yet to solve this problem.

CITATION LIST

Patent Documents

Patent Document 1: JP-A No. 2009-11377
Patent Document 2: JP-A No. 2011-177309

SUMMARY OF INVENTION

Technical Problem

A major object of the present invention is to provide a disposable diaper in which the waist side of the absorber is less influenced by the deformation of the absorber at the crotch portion and the waist side of the absorber is likely to be rounded along the surface of the wearer's body.

Solution to Problem

The present invention having solved the foregoing problem is as follows:

<The Invention of Claim 1>

A disposable diaper including a crotch portion; a ventral-side portion extending toward the ventral side of the crotch portion; a dorsal-side portion extending toward the dorsal side of the crotch portion; and an absorber in the crotch portion, the ventral-side portion, and the dorsal-side portion, wherein the absorber is divided in a front-back direction by a width-direction slit continuing in the width direction provided on at least one of front and back sides of the crotch portion, and a concave portion recessed toward the waist side is formed in width-direction centers of waist-side edge of the width-direction slit.

(Operation and Effect)

According to the present invention, the absorber is divided in the front-back direction by the width-direction slit continuing in the width direction provided on at least one of the front and back sides of the crotch portion, whereby the deformation of the absorber at the crotch portion is unlikely to exert influence on the waist side of the width-direction slit. In addition, since the concave portion recessed toward the waist side is formed in the width-direction centers of the waist-side edge of the width-direction slit, the waist-side portion of the width-direction slit in the absorber is independently deformable (under less influence of the deformation of the crotch portion), and the concave portion is deformed in such a manner as to close (the width-direction both side edges of the concave portion are closer to each other), whereby the absorber with the concave portion is likely to be rounded along the surface of the wearer's body. As a result, when the flat-shaped absorber is deformed along the surface shape of the wearer's body, it is possible to obtain a more favorable fit, prevent leakage, and improve a wearing feeling.

<The Invention of Claim 2>

The disposable diaper according to claim 1, wherein the concave portion is shaped in such a manner as to be narrower with increasing proximity to the waist side.

(Operation and Effect)

When the concave portion is shaped as described above, the concave portion is likely to deform in such a manner as to close, and the gap in the absorber with the closed concave portion is decreased.

<The Invention of Claim 3>

The disposable diaper according to claim 1 or 2, including concave portion deformation elastic members that exert a contraction force in a direction in which the width-direction both side edges of the concave portion are closer to each other.

(Operation and Effect)

Providing the concave portion deformation elastic members makes it possible to facilitate the deformation of the concave portion in such a manner as to close, and maintain elastically the concave portion in the closed state.

<The Invention of Claim 4>

The disposable diaper according to claim 3, wherein the concave portion deformation elastic members are elongated elastic members that are arranged in such a manner as to curve toward the crotch portion and cross over the concave portion.

(Operation and Effect)

Setting the concave portion deformation elastic members as elongated elastic members arranged in a curve as described above facilitates the deformation of the concave portion in such a manner as to close, and further increase the action of maintaining elastically the concave portion in the closed state. This is especially suitable for the invention of claim 2 in which the concave portion is narrower with increasing proximity to the waist side.

<The Invention of Claim 5>

The disposable diaper according to claim 3 or 4, including an outer body constituting individually or integrally a front panel and a back panel, and an inner body that includes an absorber and is attached on the inner side of the outer body ranging from the front panel to the back panel, the outer body of the front panel and the outer body of the back panel being joined together at both side edges to form side seal portions, thereby forming a waist opening and a pair of right and left leg openings, wherein fit elastic members are provided in the outer body from one side seal portion to the other side seal portion, and some of the fit elastic members are arranged as the concave portion deformation elastic members in such a manner as to cross over the concave portion.

(Operation and Effect)

In general, the outer body of an underpants-type disposable diaper is provided with elastic members to improve a fit. Accordingly, it is preferred to form the concave portion deformation elastic members from the elastic members.

<The Invention of Claim 6>

The underpants-type disposable diaper according to claim 5, wherein the fit elastic members are finely cut at least in width-direction intermediate portions in a region overlapping the inner body except portions constituting the concave portion deformation elastic members.

(Operation and effect)

It is desirable to prevent unnecessary contraction of the inner body caused by the fit elastic members in the underpants-type disposable diaper. Accordingly, it is preferable that the fit elastic members are finely cut, losing the elasticity at least in the width-direction intermediate portions in the region overlapping the inner body except the portions constituting the concave portion deformation elastic members described above.

<The Invention of Claim 7>

The disposable diaper according to any one of claims 1 to 6, wherein at least one of the width-direction slits is formed in such a manner that the clearance width becomes larger with increasing proximity to the width-direction both sides.

(Operation and Effect)

The width-direction slit may be continuous with the equal interval width in the width direction. However, when the width-direction slit is formed in such a manner that the interval width becomes larger with increasing proximity to the width-direction both sides, the concave portion is further deformed in such a manner as to close, and the absorber with the concave portion is preferably likely to be rounded.

<The Invention of Claim 8>

The underpants-type disposable diaper according to any one of claims 1 to 7, wherein an easily folded portion extending in a front-back direction is formed in a width-direction center of a crotch absorber.

(Operation and Effect)

In some of disposable diapers, an easily folded portion such as a slit or an embossed portion may be provided in the width-direction center of the absorber to improve a fit, liquid diffusibility, and the like. In that case, the conventional absorber might be deformed due to the easily folded portion to exert influence on the ventral-side portion and the dorsal-side portion. However, the absorber in the present invention exerts less influence. The easily folded portion means a portion in a folded position such as a slit, an embossed portion, or a step in a two-layer structure.

Advantageous Effects of Invention

As described above, according to the present invention, it is possible to produce the advantage of providing the disposable diaper in which the deformation of the absorber at the crotch portion is unlikely to exert influence on the absorber on the waist side, and the absorber on the waist side is likely to be rounded along the surface of the wearer's body, and others.

BRIEF DESCRIPTION OF THE DRAWINGS

FIG. 14 is a plane view of major components of the absorber.

DESCRIPTION OF EMBODIMENT

Figure 1:
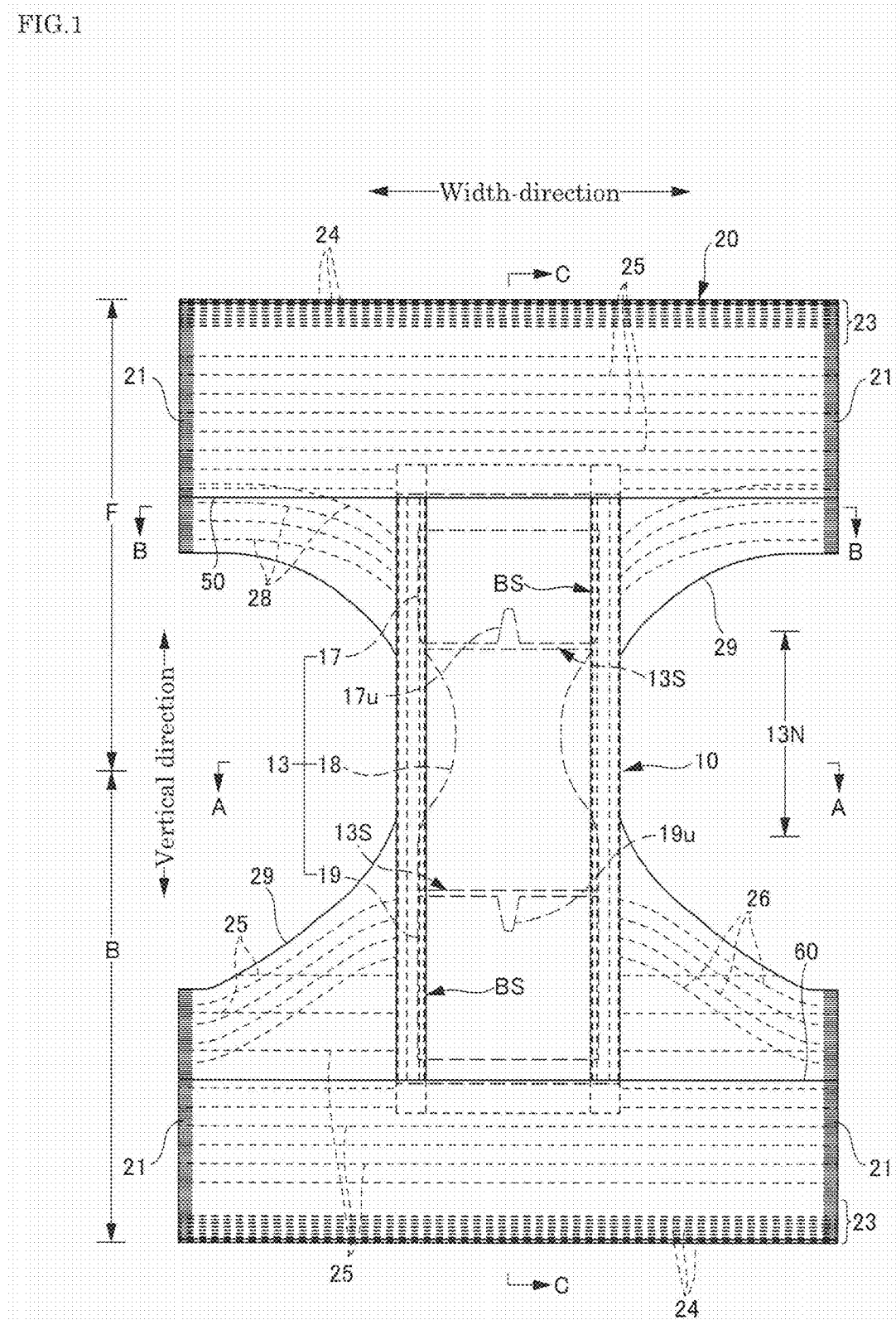
FIG. 1 is a plane view (inner surface side) of an underpants-type disposable diaper in a developed state.

One embodiment of the present invention will be described in detail with reference to the accompanied drawings. The "extension ratio" herein takes on a value relative to the natural length as 100%. The dot patterns in the drawings represent a joining means such as a hot-melt adhesive.

FIGS. 1 to 7 illustrate underpants-type disposable diaper. The underpants-type disposable diaper (hereinafter, also simply called diaper) has an outer body 20 constituting integrally a front body F and a back body B and an inner body 10 fixed to the inner surface of the outer body 20 ranging from the front body F to the back body B. The inner body 10 is formed by interposing an absorber 13 between a liquid pervious face sheet 11 and a liquid impervious back sheet 12. In manufacturing, the back surface of the inner body 10 is joined to the inner surface (upper surface) of the outer body 20 by a joining means such as a hot-melt adhesive (as illustrated in the dot-patterned part of FIG. 2), then the inner body 10 and the outer body 20 are folded in the center in the vertical (front-back) direction as a boundary between the front body F and the back body B, and then the both side parts are joined together by heat welding, a hot-melt adhesive, or the like to form side seal portions 21, thereby obtaining the underpants-type disposable diaper having a waist opening and a pair of right and left leg openings.

(Structure Example of the Inner Body)

Figure 4:
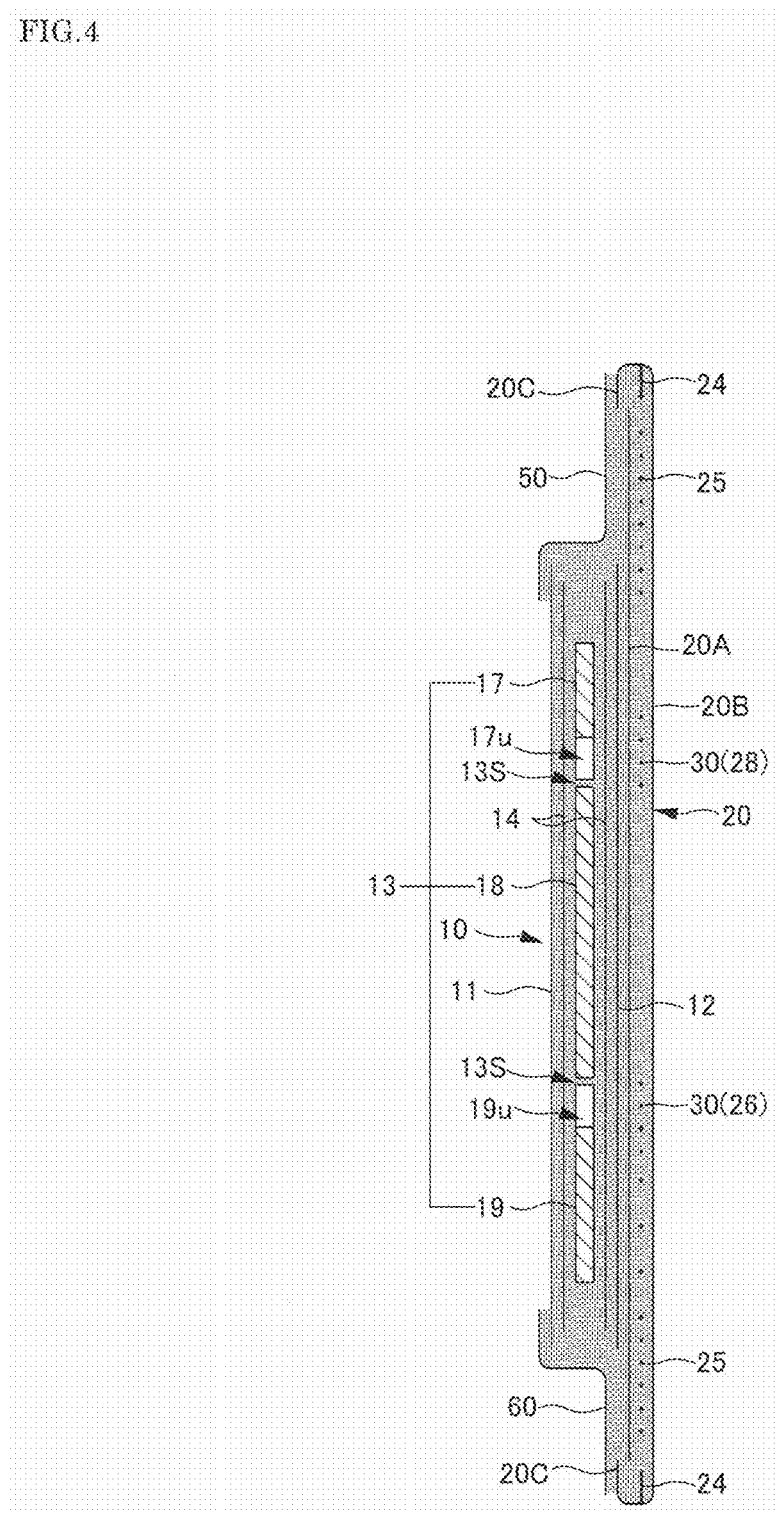
FIG. 4 is a cross-sectional view of FIG. 1 taken along line C-C.
Figure 5:
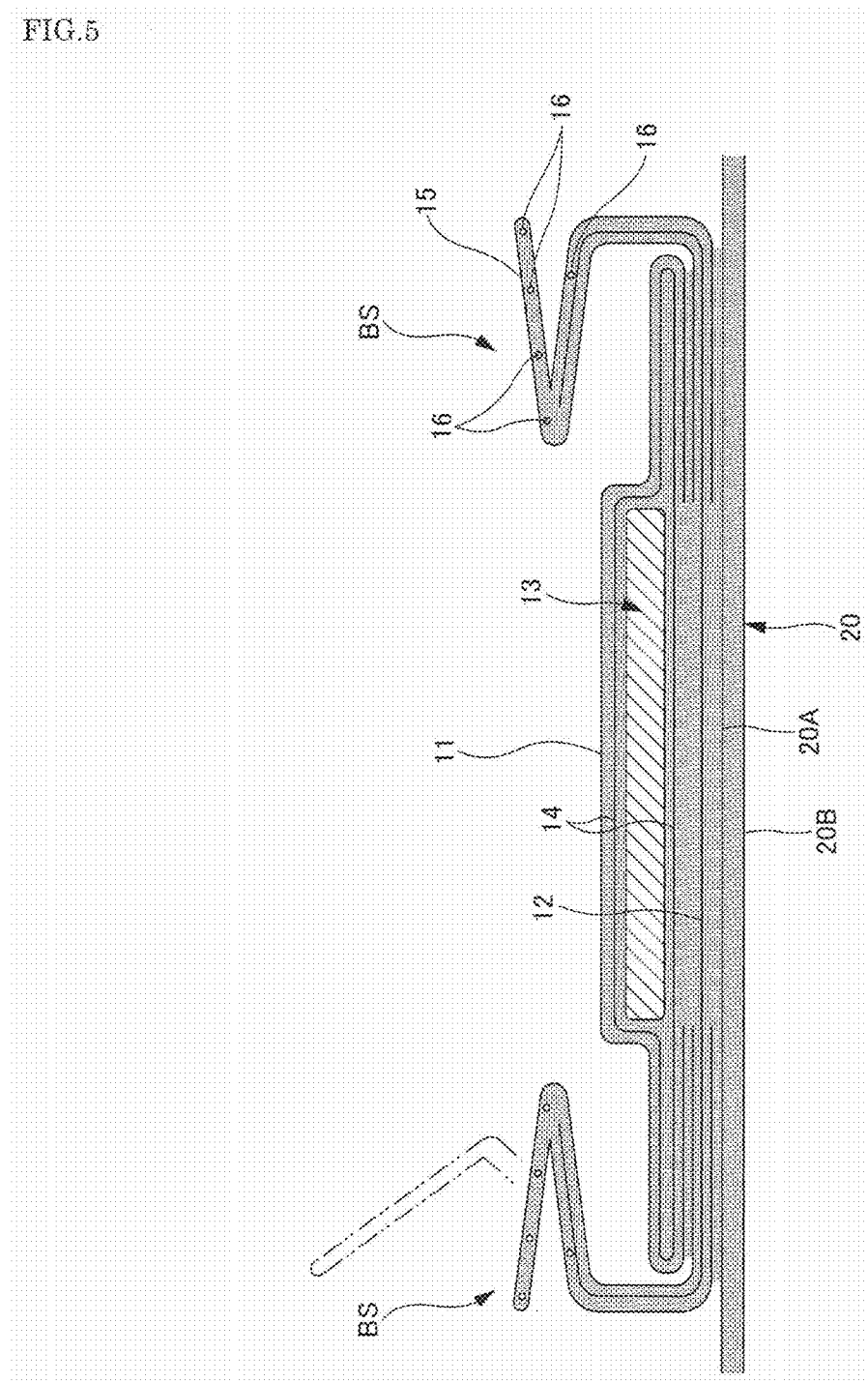
FIG. 5 is a cross-sectional view of FIG. 1 taken along line A-A.
Figure 6:
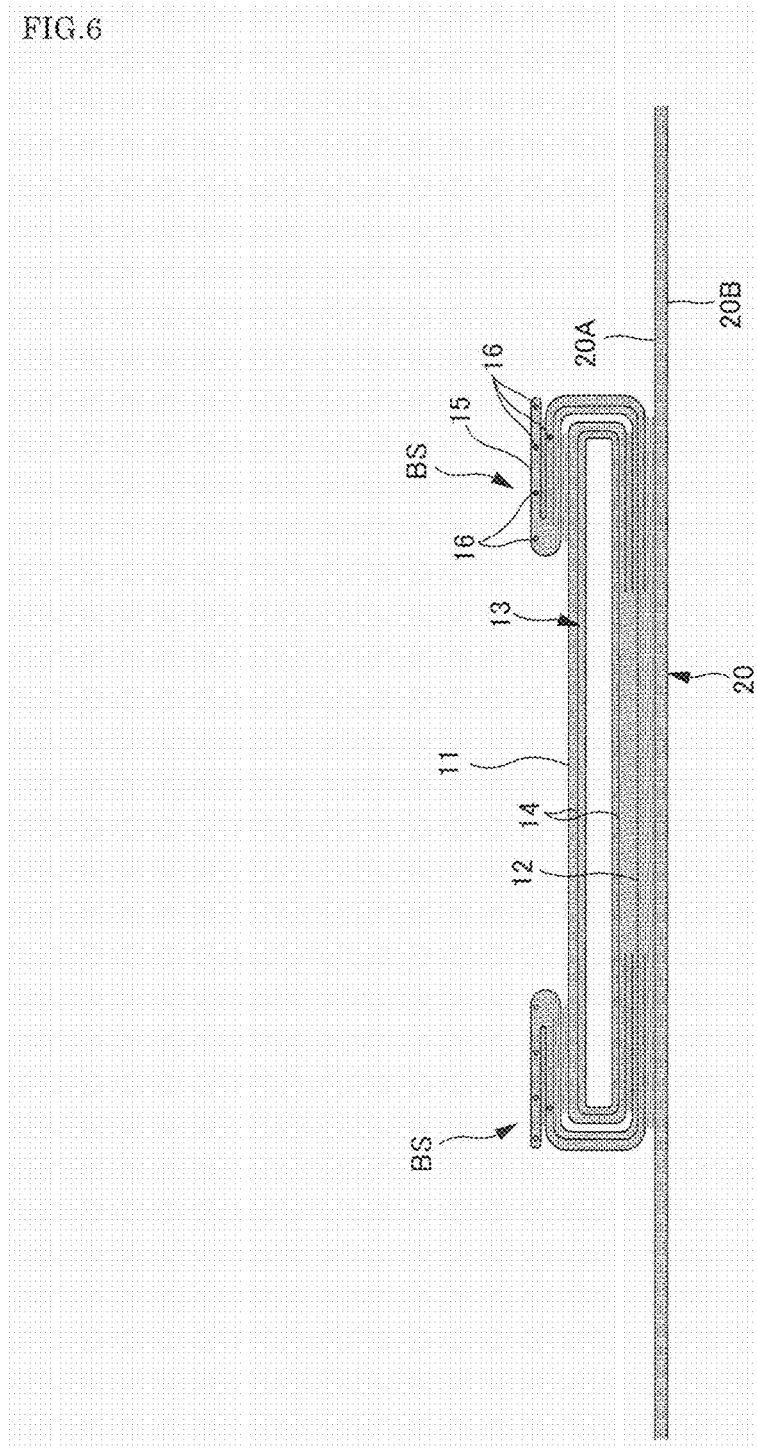
FIG. 6 is a cross-sectional view of FIG. 1 taken along line B-B.
Figure 7:
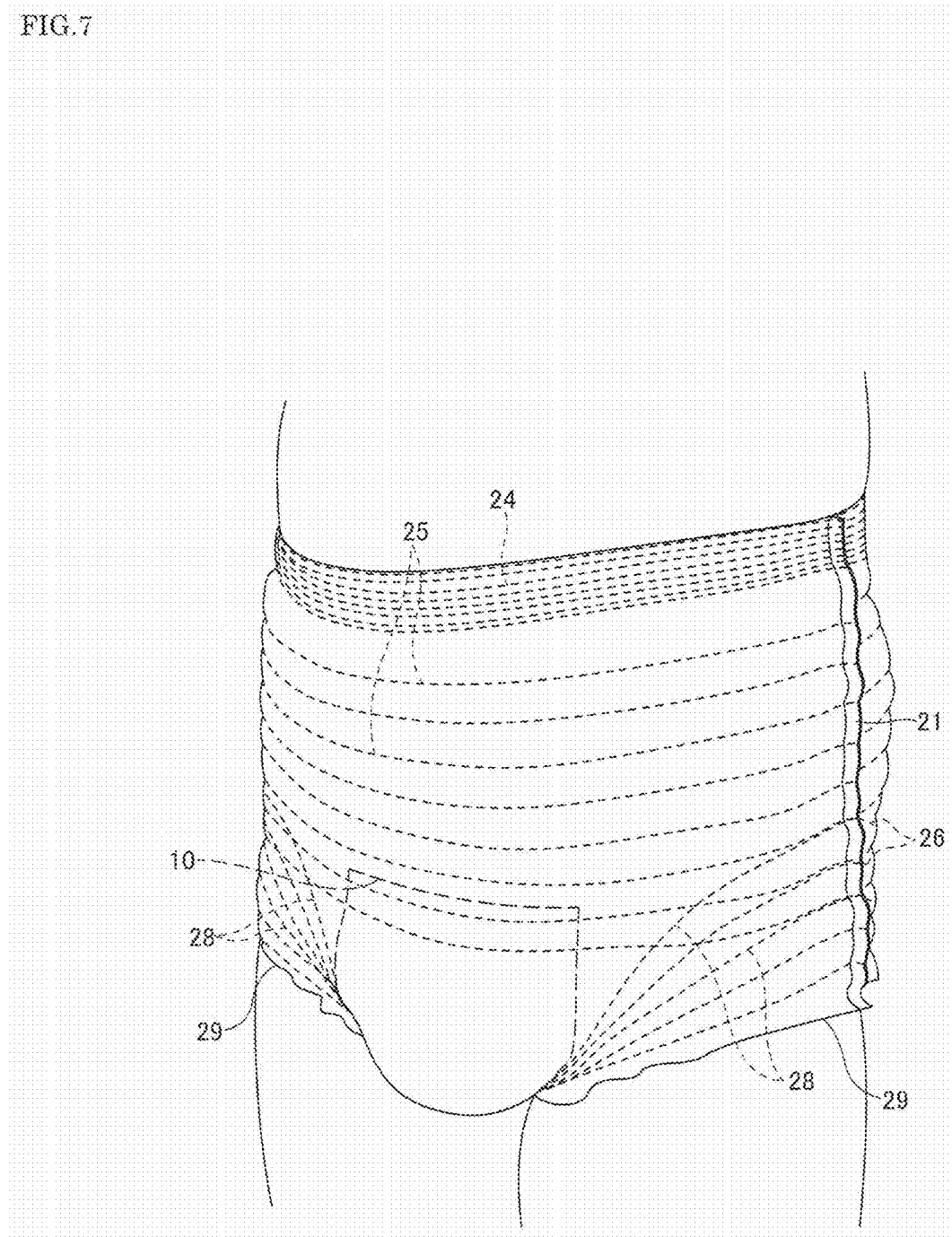
FIG. 7 is a perspective view of the underpants-type disposable diaper in a worn state.

As illustrated in FIGS. 4 to 6, the inner body 10 is structured such that the absorber 13 is interposed between the liquid pervious face sheet 11 made of non-woven fabric or the like and the liquid impervious back sheet 12 made of polyethylene or the like. The inner body 10 is intended to absorb and hold excretion having passed through the face sheet 11. Although there is no particular limitation on the planar shape of the inner body 10, the inner body 10 is generally shaped in an approximate rectangle as in the illustrated drawing.

The liquid pervious face sheet 11 covering the external side (skin-contacting side) of the absorber 13 is preferably a porous or non-porous non-woven fabric sheet or a porous plastic sheet. The raw fibers for non-woven fabric may be synthetic fibers based on olefin such as polyethylene or polypropylene, or synthetic fibers based on polyester or polyamide, or reproduced fibers of rayon or cupra, natural fibers of cotton or the like. The non-woven fabric may be produced by any appropriate processing method such as spun-lacing, spun-bonding, thermal bonding, melt-blowing, or needle punching. Among these processing methods, the spun-lacing method is excellent for flexibility and drape properties, and the thermal bonding method is excellent for bulkiness and softness. Forming a large number of through holes in the liquid pervious face sheet 11 would allow quick absorption of urine and the like and produce an excellent feeling of dryness. The liquid pervious face sheet 11 wraps around the side edges of the absorber 13 and extends up to the back surface of the absorber 13.

The liquid impervious back sheet 12 covering the back side (non-skin-contacting side) of the absorber 13 is made of a liquid impervious plastic sheet of polyethylene, polypropylene, or the like. However, in recent years, the liquid impervious plastic sheets with moisture perviousness have been used preferably from the viewpoint of prevention of stuffiness. The liquid impervious and moisture pervious sheet is a microporous sheet that is obtained by melting and kneading an inorganic filling agent in an olefin resin such as polyethylene, polypropylene, or the like to form a sheet and then elongating the sheet in a uniaxial or biaxial direction, for example.

The absorber 13 is basically made from a publicly known material, for example, accumulated pulp fibers, a filament assembly of cellulose acetate or the like, or non-woven fabric. The absorber 13 may include as necessary high-absorbent polymer particles mixed and fixed thereto. The absorber 13 can be wrapped as necessary with a package sheet 14 with liquid perviousness and liquid retention such as crepe paper for retention of the shape and the polymer.

The absorber 13 is shaped as a whole like a sand glass with a narrower part 13N smaller in width than the front and back sides of the crotch portion. However, the absorber 13 may have an arbitrary shape such as a rectangle. The dimensions of the narrower part 13N can be decided as appropriate. However, the length in the front-back direction of the narrower part 13N can be about 20 to 50% of the entire length of the diaper. The smallest width of the narrower part 13N can be about 40 to 60% of the entire width of the absorber 13. When the planar shape of the inner body 10 is an approximate rectangle with the narrower part 13N as described above, in the inner body 10, remaining parts without the absorber 13 are formed according to the narrower part 13N of the absorber 13.

The inner body 10 has three-dimensional gathers BS fitting around the legs on the both sides. As illustrated in FIGS. 5 and 6, each of the three-dimensional gathers BS is formed with a gather nonwoven fabric 15 as a two-folded duplicate sheet including a fixation portion fixed to the side of the back surface of the inner body, a main unit portion extending from the fixation portion through the lateral side of the inner body to the side part of the front surface of the inner body, lying down portions formed by fixing the front end and back end of the main unit portion in a lying down state to the side parts of the front surface of the inner body, and a free portion formed in an un-fixed state between the lying down portions.

Elongated gather elastic members 16 are arranged at forward ends of the free portion in the duplicate sheet. The gather elastic members 16 are intended to stand the nonwoven fabric portions protruding from the side edges of the absorber by their elastic stretching force as illustrated by the two-dot chain line in FIG. 5 to form the three-dimensional gathers BS in the product state.

The liquid impervious back sheet 12 enters the inside of the duplicate sheet-type gather nonwoven fabric 15 to constitute a leakage prevention wall on the lower end side of the three-dimensional gathers BS as illustrated in FIG. 5. The liquid impervious back sheet 12 is desirably opaque so as not to allow the dark color of stool and urine to be seen through. To make the opaque liquid impervious back sheet 12, plastic is preferably formed into a film with internal addition of pigments and fillers such as calcium carbonate, titanium oxide, zinc oxide, white carbon, clay, talc, and barium sulfate.

The gather elastic members 16 can be made from a generally used material such as styrene-based rubber, olefin-based rubber, urethane-based rubber, ester-based rubber, polyurethane, polyethylene, polystyrene, styrene-butadiene, silicon, or polyester. To make the gather elastic members 16 hard to see from the outside, it is preferable that the gather elastic members 16 have a thickness of 925 dtex or less and are arranged under a tension of 150 to 350% at intervals of 7.0 mm or less. The gather elastic members 16 may be a thread type as illustrated in the drawing or a tape type with a certain width.

As the liquid pervious face sheet 11, the raw fibers for the gather nonwoven fabric 15 may be synthetic fibers based on olefin such as polyethylene or polypropylene, polyester, polyamide, or reproduced fibers of rayon or cupra, natural fibers of cotton or the like. The non-woven fabric may be produced by any appropriate processing method such as spun-bonding, thermal bonding, melt-blowing, or needle punching. However, in particular, the non-woven fabric with low basis weight and high air permeability is preferably used for the gather nonwoven fabric 15 for prevention of stuffiness. Further, the three-dimensional gather sheets 15 are desirably made from water-repellent non-woven fabric coated with a silicon-based, paraffin metal-based, or alkyl electrochromic chloride-based water repellent agent to prevent passage of urine or the like and rash on the wearer's body, and enhance the feel and texture (feeling of dryness).
(Structure Example of the Outer Body)

The outer body 20 has a two-layer structure composed of a press sheet 20A and a back sheet 20B made of non-woven fabric or the like as illustrated in FIGS. 4 to 6. Various elastic members are disposed to impart elasticity between the press sheet 20A and the back sheet 20B and between the non-woven fabric sheets in folded portions 20C formed by folding the waist opening edges of the back sheet 20B toward the inner surface side. The planar shape of the outer body 20 is an approximate sand glass as a whole due to concave leg lines 29 formed on the both sides of the intermediate portion to make the leg openings. To reduce costs and improve the air permeability of the crotch portion, the press sheet 20A and the back sheet 20B may be divided into two in the front-back direction so that these sheets are arranged to be separated from each other at the crotch portion, or either the press sheet 20A or the back sheet 20B may be divided into two in the front-back direction so that the divided sheets are separated from each other at the crotch portion and the single sheet is positioned at the crotch portion.

Figure 2:
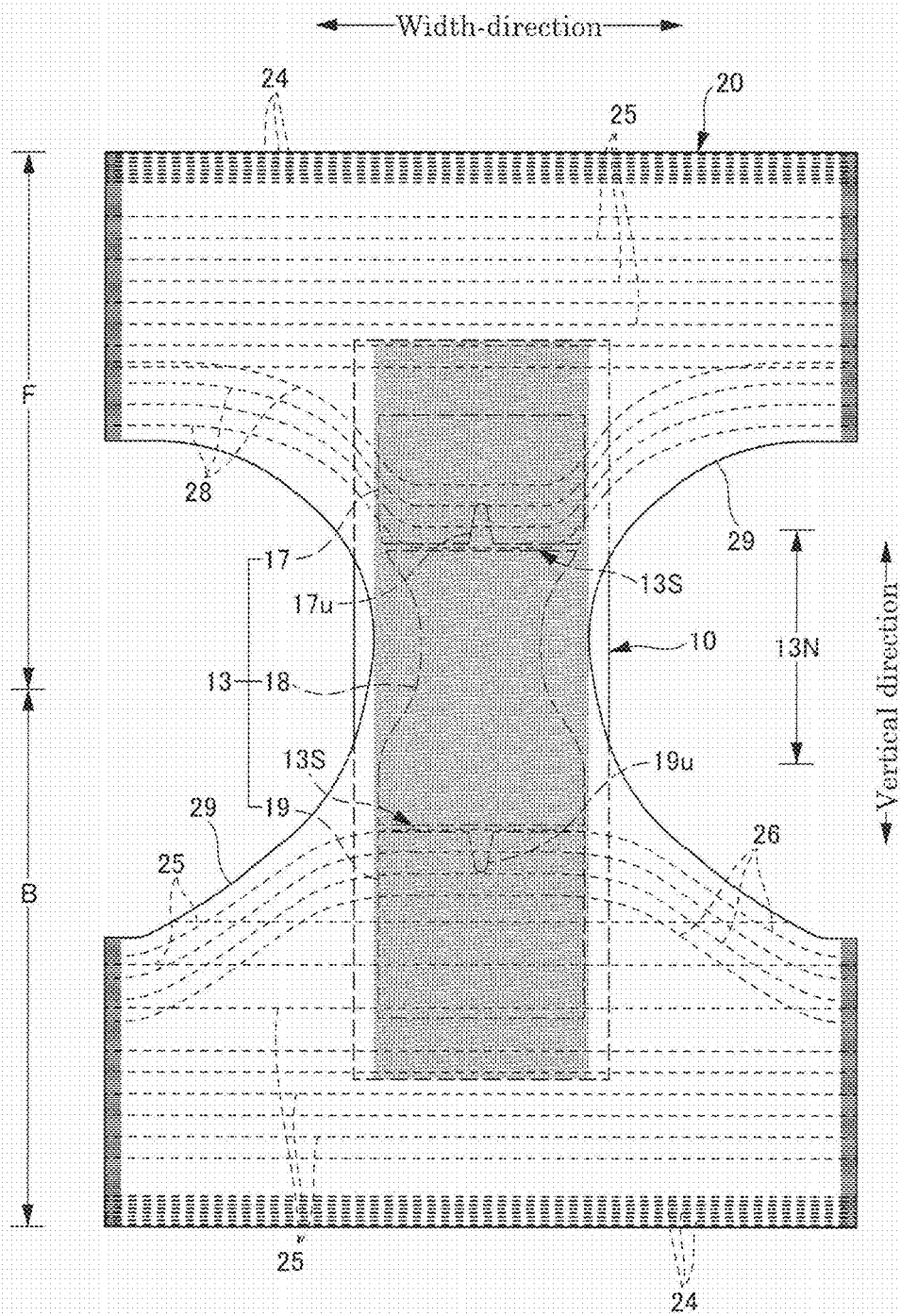
FIG. 2 is a plane view (outer surface side) of the underpants-type disposable diaper in the developed state.
Figure 3:
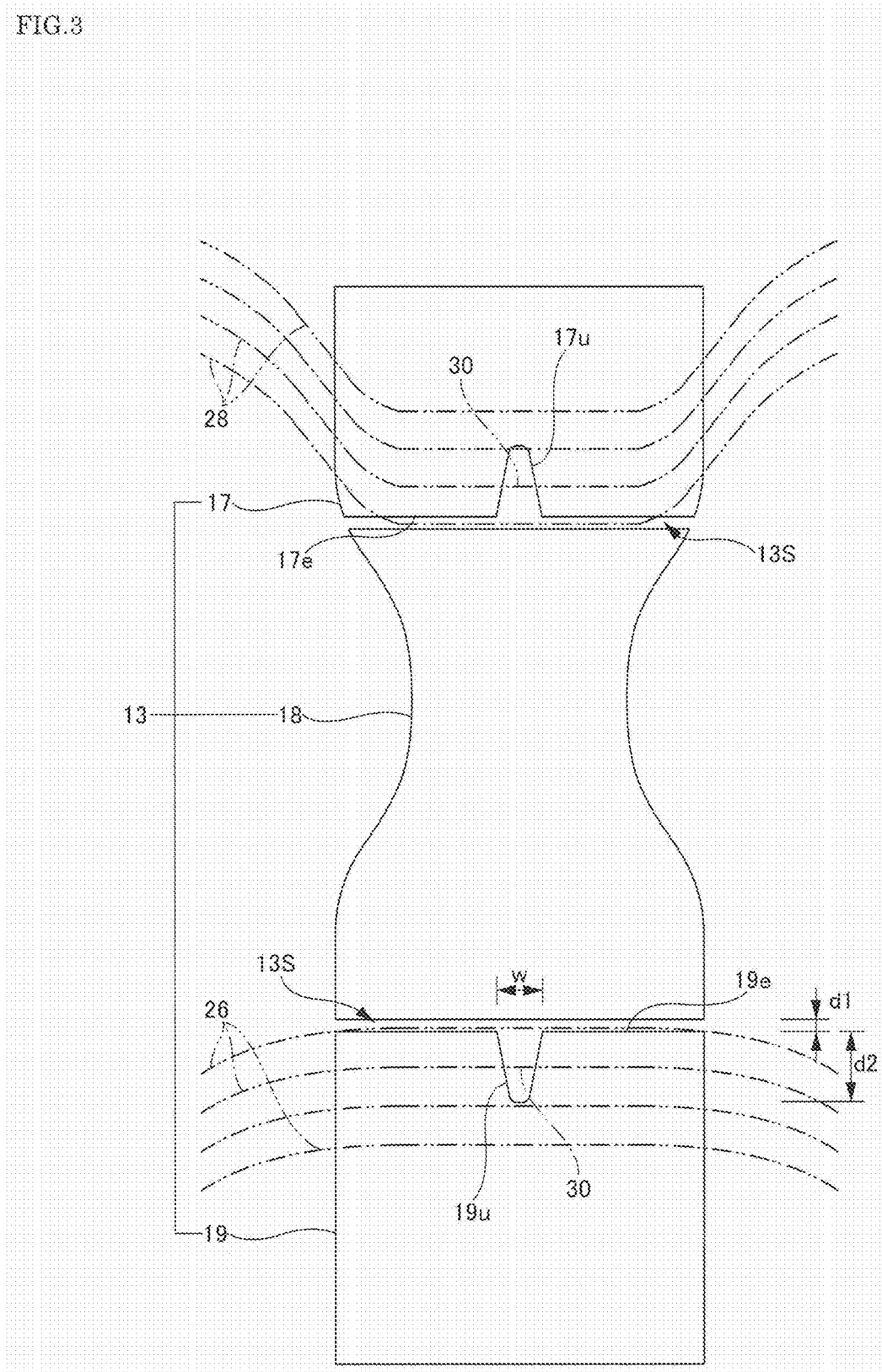
FIG. 3 is a plane view of major components of an absorber.

In the illustrated mode, the outer body 20 has, as elastic members, waist portion elastic members 24 arranged in the waist opening 23 and its neighborhood and a plurality of waist lower portion elastic members 25 arranged in a width direction at vertical intervals in the front panel F and the back panel B in the developed state illustrated in FIGS. 1 to 3. Besides, the outer body 20 includes a plurality of curved elastic members 26 and 28 that is arranged at intervals without crossing each other and are curved and extended in the front panel F and the back panel B in a pattern ranging from one side seal portion 21 to the crotch portion along one leg opening, crossing over the crotch portion, and reaching the other side seal portion 21 along the other leg opening. These elastic members 24 to 28 are fixed in the state extended at a predetermined stretch rate along their extending directions. Incidentally, the outer body 20 has no leg elastic members that continue from the side seal portions of the front panel F to the side seal portions of the back panel B along the leg lines 29 but the outer body 20 may have such leg elastic members (not illustrated).

The waist portion elastic members 24 are a plurality of elongated elastic members such as rubber threads arranged at vertical intervals at the waist opening edge and its neighborhood in the zones of the side seal portions 21 where the front panel F and the back panel B are joined together, and are intended to impart a stretching force to tighten the wearer's waist to attach the diaper to the wearer's body. The waist portion elastic members 24 in the illustrated example are formed by the use of rubber threads but may be tape-like stretchable members, for example. In addition, the waist portion elastic members 24 in the illustrated example are sandwiched in the non-woven fabric sheets of the folded portions 20C of the back sheet 20B at the waist portion.

Alternatively, the waist portion elastic members 24 may be sandwiched between the press sheet 20A and the back sheet 20B.

The waist lower portion elastic members 25 are a plurality of elongated elastic members such as rubber threads arranged at vertical intervals in the zones of the side seal portions 21 ranging generally from the upper to lower sides, and are intended to impart width-direction stretching force to the waist portions of the front panel F and the back panel B to allow the diaper to be closely attached to the wearer's body. The differentiation between the waist portion elastic members 24 and the waist lower portion elastic members 25 may not necessarily be clear. For example, of the elastic members arranged in the width direction at vertical intervals in the front panel F and the back panel B, some of the upper-side elastic members may serve as waist portion elastic members, although the number of the waist portion elastic members cannot be specified, and the remaining elastic members may serve as waist lower portion elastic members.

The dorsal-side curved elastic members 26 disposed separately from the waist lower portion elastic members 25 in the back panel B are elongated elastic members such as rubber threads that are arranged along predetermined curve lines. The number of the dorsal-side curved elastic member 26 may be one but is preferably plural. In the illustrated example, the dorsal-side curved elastic members 26 are four elongated elastic members such as rubber threads. These dorsal-side curved elastic members 26 are arranged at intervals without crossing each other. The dorsal-side curved elastic members 26 are not arranged as a substantially single bundle of about two or three members at close intervals but three or more, preferably four or more members are arranged at intervals of about 3 to 20 mm, preferably about 6 to 16 mm to form a predetermined stretchable zone.

The ventral-side curved elastic members 28 disposed separately from the waist lower portion elastic member group 25 in the front panel F of the outer body 20 are elongated elastic members such as rubber threads arranged along predetermined curved lines. The number of the ventral-side curved elastic member 28 may be one but is preferably plural. In the illustrated example, the ventral-side curved elastic members 28 are four thread-like elastic members. These ventral-side curved elastic members 28 are arranged at intervals without crossing each other. The ventral-side curved elastic members 28 are not arranged as a substantially single bundle of about two or three members at close intervals but three or more, preferably four or more members are arranged at intervals of about 3 to 20 mm, preferably about 6 to 16 mm to form a predetermined stretchable zone.

Figure 8:
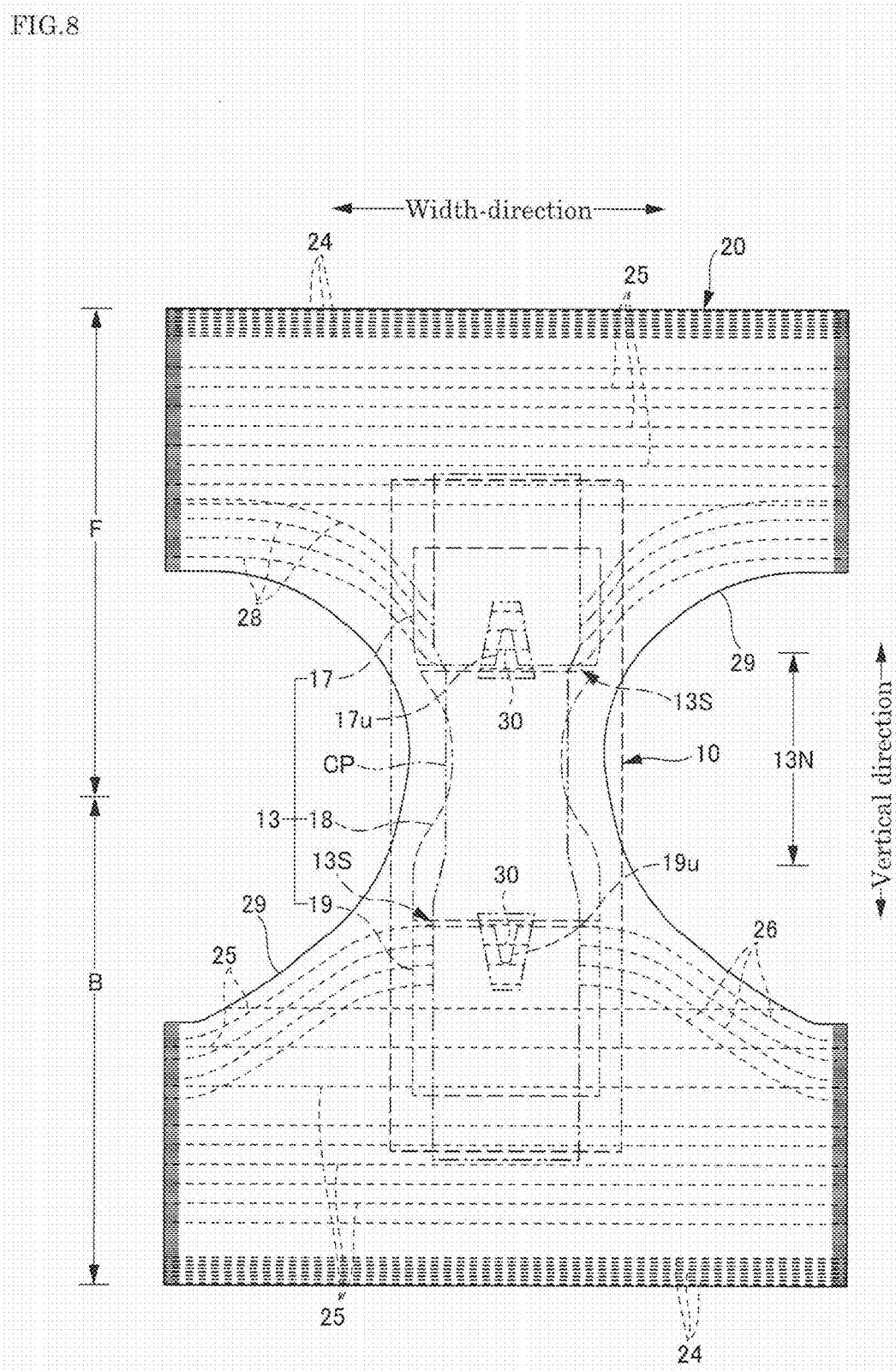
FIG. 8 is a plane view of a cut pattern of elastic members.

As understood from FIG. 8 described later, after the waist lower portion elastic members 25 and the curved elastic members 26 and 28 are arranged in the front panel F and the back panel B and continuously fixed to the outer body at the time of manufacture, some or all of the elastic members overlapping the inner body may be finely cut in a predetermined cutting pattern CP to form a non-contraction part on which no contraction force acts (that is, the part overlapping the cutting pattern CP in FIG. 8), and form parts extending laterally from the non-contraction part as contraction parts on which contraction force acts (that is, the parts where the waist lower portion elastic members 25 and the curved elastic members 26 and 28 are left in the continuous state on the lateral sides of the cutting pattern CP in FIG. 8). Accordingly, when being continuously provided from one side seal portion 21 to the other (opposite) side seal portion 21 crossing over the inner body 10, some or all of the waist lower portion elastic members 25 and the curved elastic members 26 and 28 overlapping the inner body 10 are finely cut. This prevents unnecessary width-direction contraction of the inner body (especially the absorber 13). As a matter of course, the waist lower portion elastic members 25 and the curved elastic members 26 and 28 may be arranged continuously crossing over the inner body 10.

The outer body 20 can be manufactured by the technique described in JP-A No. 4-28363 or JP-A No. 11-332913, for example. In addition, the curved elastic members 26 and 28 can be preferably cut and made discontinuous on the inner body 10 by employing the cutting technique described in JP-A No. 2002-35029, JP-A No. 2002-178428, or JP-A No. 2002-273808.

Unlike in the illustrated example, the curved elastic members 26 and 28 may be provided only in either of the front body F and the back body B. When the curved elastic members 26 and 28 are provided in both the front body F and the back body B, some or all of the group of curved elastic members 28 arranged in the front body F and some or all of the group of curved elastic members 26 arranged in the back body B may cross each other (not illustrated). However, in a preferred mode, the group of curved elastic members 28 arranged in the front body F and the group of curved elastic members 26 arranged in the back body B do not cross each other, but separate from each other in the vertical direction at the intermediate portion in the front-back direction, in particular, at the position slightly closer to the front body F.

Further, the curved elastic members 26 and 28 may not be curved entirely and may have linear parts.

The extension ratios of the elastic members 24 to 28 in attaching can be decided as appropriate. However, for a general diaper for adults, the extension ratio of the waist portion elastic members 24 can be about 160 to 320%, the extension ratio of the waist lower portion elastic members 25 can be about 230 to 320%, and the extension ratio of the curved elastic members 26 and 28 can be about 230 to 320%.

(Front and Back Pressing Sheets)

As also illustrated in FIGS. 1 and 4, front and back pressing sheets 50 and 60 are provided to cover the front and back end portions of the inner body 10 on the inner surface of the outer body 20 and prevent leakage from the front and back edges of the inner body 10. The illustrated mode will be described more in detail. The front pressing sheet 50 extends on the inner surface of the front body F in the width direction entirely from the inner surface of the folded portion 20C at the waist-side end to the part overlapping the front end part of the inner body 10. The back pressing sheet 60 extends on the inner surface of the back body B in the width direction entirely from the inner surface of the folded portion 20C at the waist-side end to the part overlapping the back end part of the inner body 10. The front and back pressing sheets 50 and 60 can have small non-bonded portions at the entire crotch lower side edges in the width direction (or only at the central portion) to prevent the adhesive from squeezing out and allow the non-bonded portions to lift slightly from the face sheet and serve as leak prevention walls.

Attaching the front and back pressing sheets 50 and 60 as separate members as in the illustrated mode would provide the advantage of a higher degree of freedom of material selection but also provide the disadvantage of increase in the numbers of materials and manufacturing processes. Accordingly, the folded portions 20C formed by folding the outer body 20 toward the inside of the diaper may be extended up to the parts overlapping the inner body 10 to form the parts equivalent to the pressing sheets 50 and 60.

(About an Absorber Divided Structure)

Figure 9:
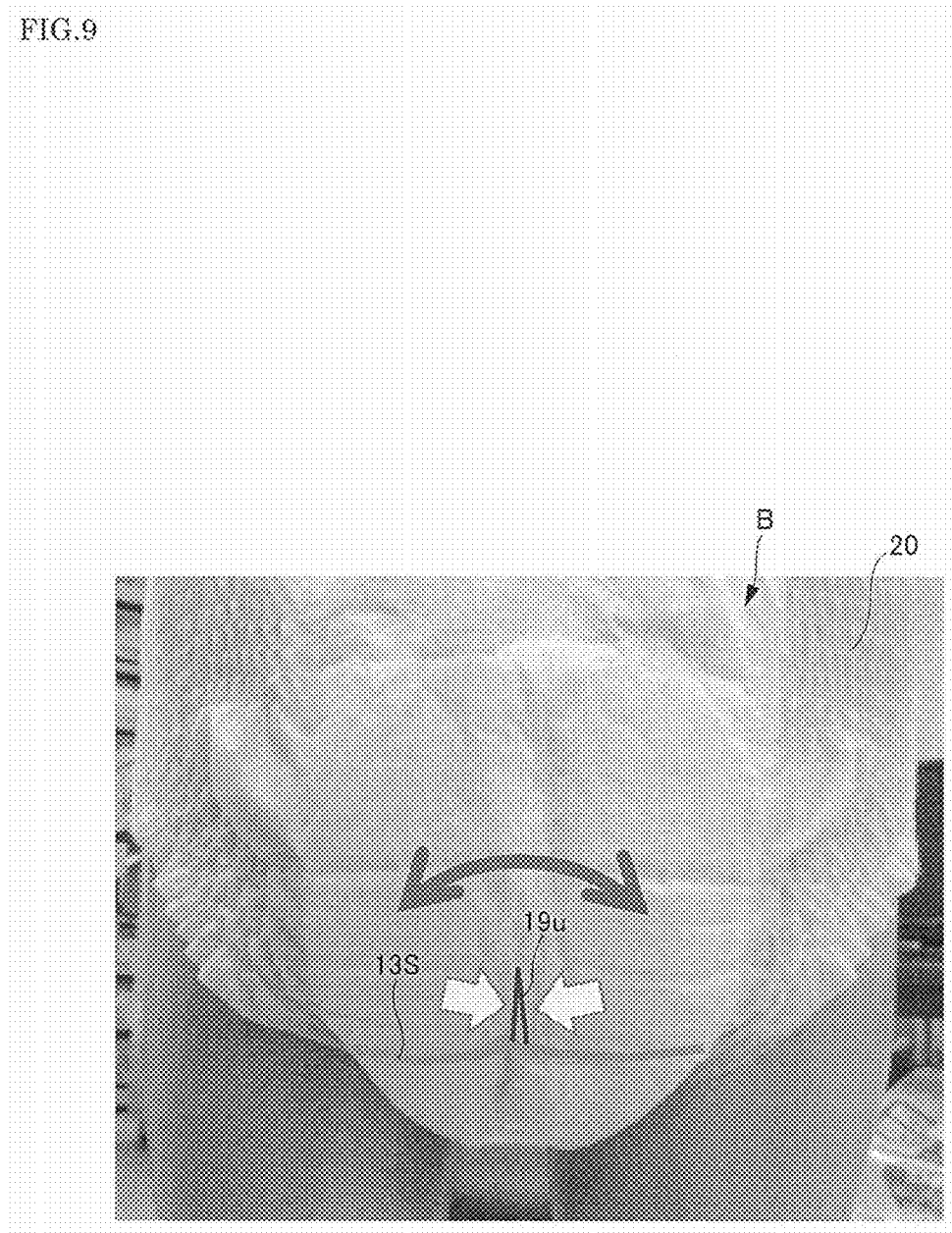
FIG. 9 is a photograph of the underpants-type disposable diaper attached to a dummy doll.
Figure 10:
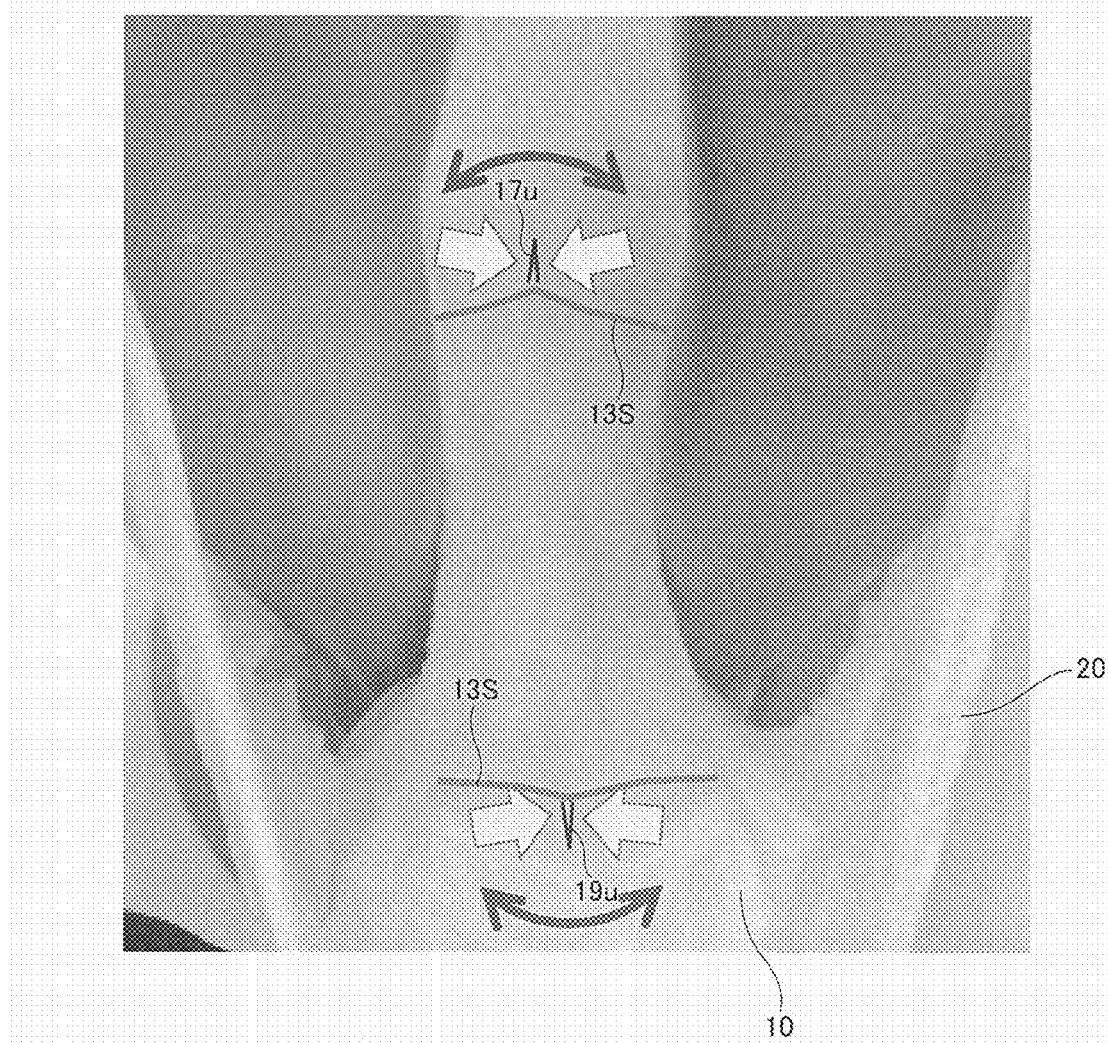
FIG. 10 is a photograph of the underpants-type disposable diaper attached to the dummy doll.

Characteristically, as illustrated in FIGS. 3 and 4, the absorber 13 is divided into a ventral-side absorber 17, a crotch-portion absorber 18, and a dorsal-side absorber 19 in the front-back direction (these absorbers are discontinuous) by width-direction slits 13S that are continuous in the width direction and provided at the boundary between the crotch portion and the ventral-side portion and at the boundary between the crotch portion and the dorsal-side portion. In addition, concave portions 17$u$ and 19$u$ recessed toward the waist side are formed in the waist-side edges of the width-direction slits 13S, specifically, in the width-direction centers of a back edge 17$e$ of the ventral-side absorber 17 and a front edge 19$e$ of the dorsal-side absorber 19. When the absorber 13 is divided into the ventral-side absorber 17, the crotch-portion absorber 18, and the dorsal-side absorber 19 by the width-direction slits 13S continuing in the width direction as described above, the deformation of the crotch-portion absorber 18 is unlikely to exert influence on the ventral-side absorber 17 and the dorsal-side absorber 19 as also understood from the state of wrinkles seen in FIG. 9. Besides, forming the concave portions 17$u$ and 19$u$ recessed toward the waist side in the width-direction centers of the waist-side edges 17$e$ and 19$e$ of the width-direction slits 13S allows the ventral-side absorber 17 and the dorsal-side absorber 19 to deform independently (under less influence of the deformation of the crotch-portion absorber 18). Accordingly, as illustrated by arrows in FIGS. 9 and 10, the concave portions 17$u$ and 19$u$ are deformed in such a manner as to close (the width-direction both side edges of the concave portions 17$u$ and 19$u$ are close to each other), and the ventral-side absorber 17 and the dorsal-side absorber 19 are deformed in a round shape along the surface of the wearer's body. As a result, when the flat-shaped absorber 13 is deformed along the surface shape of the wearer's body, it is possible to obtain a more favorable fit, prevent leakage, and improve a wearing feeling.

The positions of the width-direction slits 13S can be decided as appropriate. In general, however, when the front end position of the absorber 13 is assumed to be 0% and the back end position of the absorber 13 is assumed to be 100%, the position of the ventral-side width-direction slit 13S is preferably 15 to 40%, and the position of the dorsal-side width-direction slit 13S is preferably 50 to 80%. The width-direction slit 13S may be provided on the front and back sides of the crotch portion as in the illustrated mode or may be provided only either one of the front and back sides.

Figure 11:
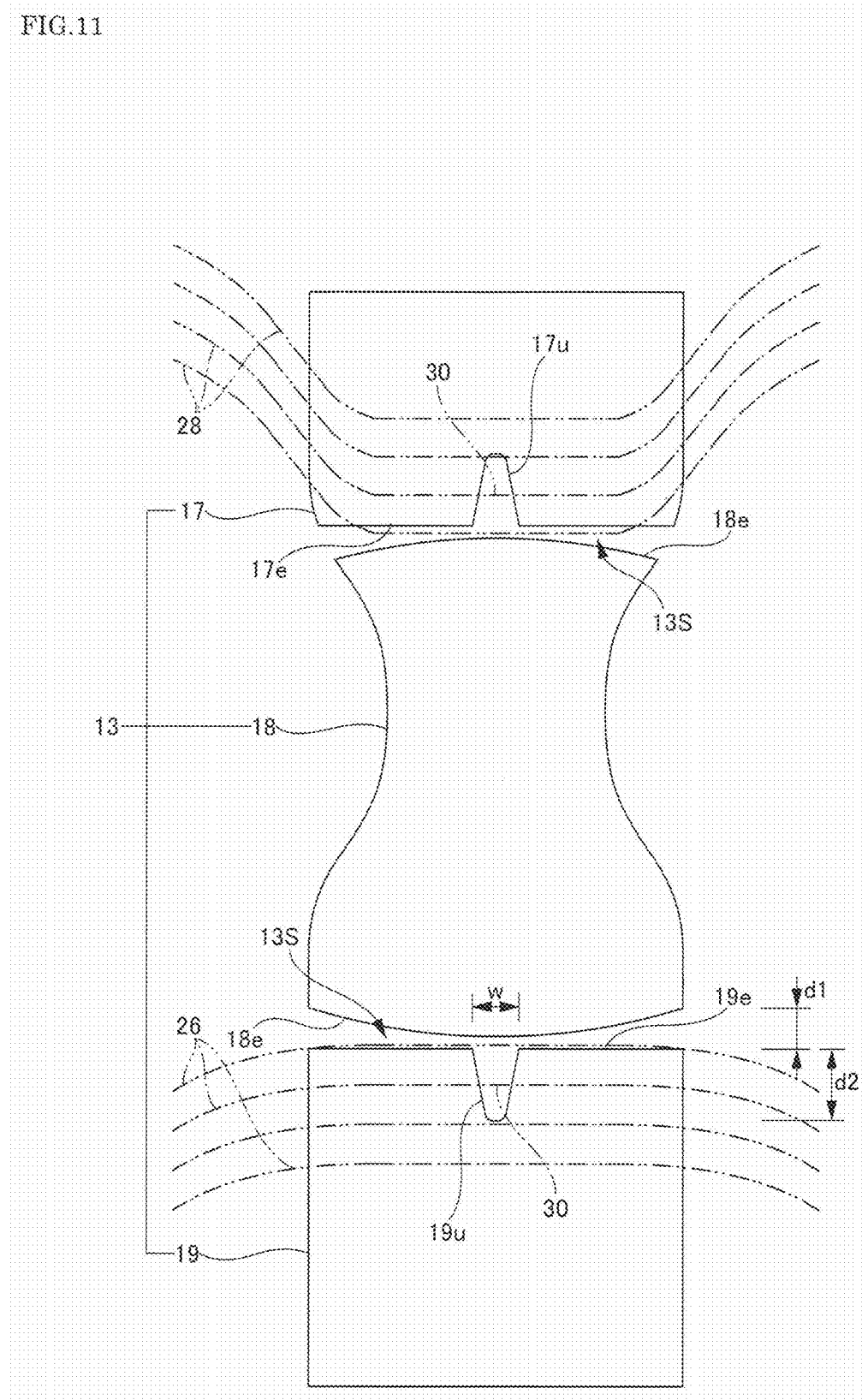
FIG. 11 is a plane view of major components of the absorber.

An interval width d1 of the width-direction slit 13S can be decided as appropriate. However, when the interval width d1 is too small, it is almost useless to provide the slit, and when the interval width d1 is too large, this results in reduction in diffusibility and absorption amount. Accordingly, the interval width d1 is preferably about 3 to 15 mm. Although the width-direction slit 13S may be continuous in the width direction at the equal interval width d1, the width-direction slit 13S is preferably formed such that the interval width d1 becomes larger with increasing proximity to the width-direction both sides as illustrated in FIG. 11, because the concave portions 17$u$ and 19$u$ are further deformed in such a manner as to close, whereby the absorber 13 having the concave portions 17$u$ and 19$u$ is likely to be rounded. When the width-direction slits 13S are provided on the front and back sides of the crotch portion, the interval width d1 may be changed in either the ventral-side width-direction slit 13S or the dorsal-side width-direction slit 13S. The change in the interval width d1 of the width-direction slit 13S may be made by curving both the waist-side edges 17e and 19e of the width-direction slits 13S and the crotch portion-side edges 18e of the width-direction slits 13S but is preferably made by curving the crotch portion-side edges 18e toward the waist side.

In the illustrated mode, the concave portions 17u and 19u are formed in both the ventral-side width-direction slit 13S and the dorsal-side width-direction slit 13S. However, even when the width-direction slits 13S are provided on the front and back sides of the crotch portion, the concave portion may be formed only in either the ventral-side width-direction slit 13S or the dorsal-side width-direction slit 13S.

Figure 12:
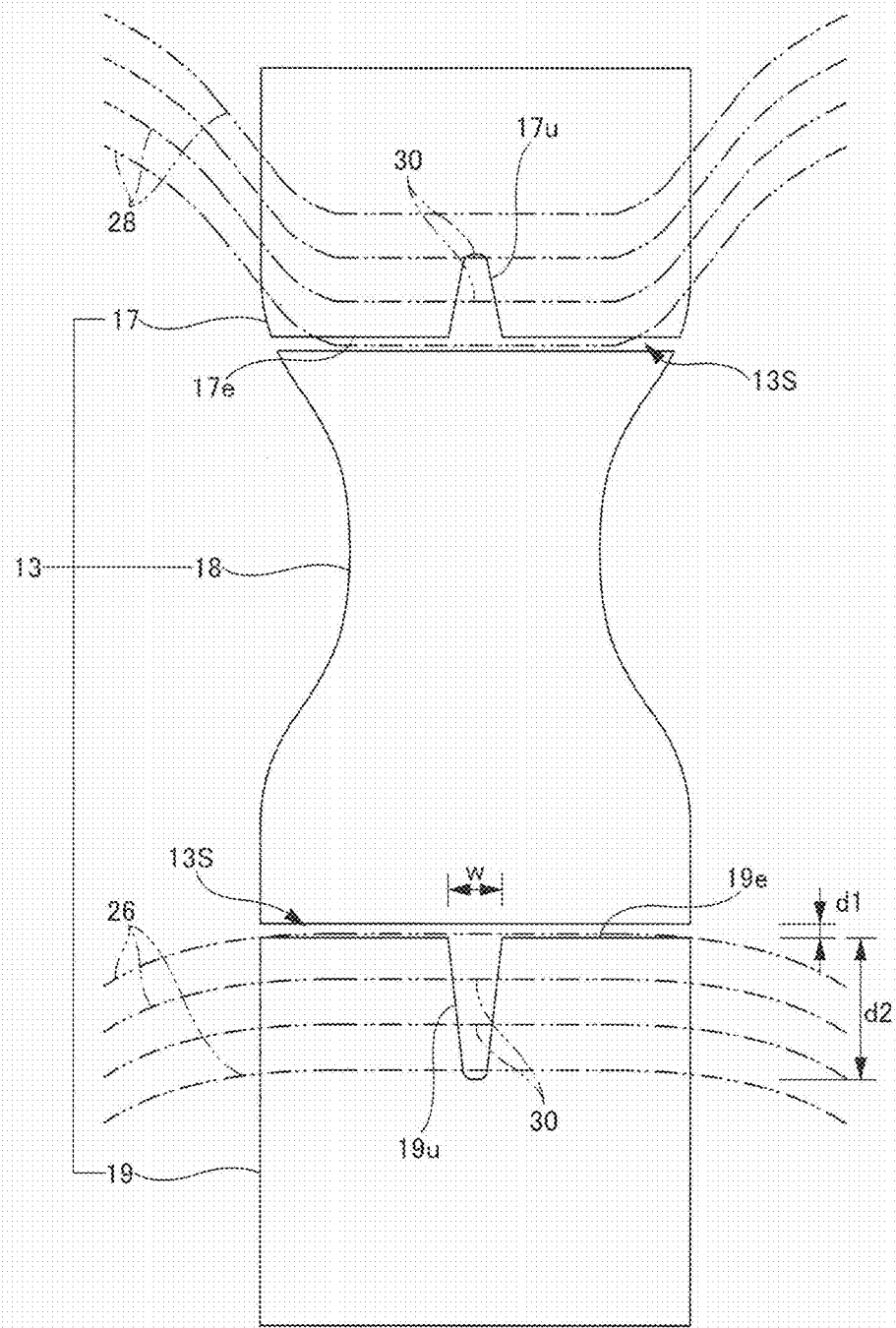
FIG. 12 is a plane view of major components of the absorber.

The shapes of the concave portions 17u and 19u can be decided as appropriate. The concave portions 17u and 19u may be formed in a rectangular shape or an inverted trapezoidal shape in which the width is larger with increasing proximity to the waist side. However, it is preferable to form the concave portions 17u and 19u in a triangular shape or a trapezoidal shape, for example, in which the width is smaller with increasing proximity to the waist side as in the illustrated mode because the concave portions 17u and 19u are likely to deform in such a manner as to close and the gaps in the absorber 13 with the closed concave portions 17u and 19u are decreased. The dimensions of the concave portions 17u and 19u can be decided as appropriate. However, each width w is preferably about 5 to 25 mm, and depth (front-back direction length) d2 is preferably about 20 to 50 mm. The concave portions 17u and 19u may be or may not be the same in the depth d2 between the ventral side and the dorsal side. In particular, as illustrated in FIG. 12, the depth d2 of the concave portion 19u on the dorsal side is preferably larger than the depth d2 of the concave portion 17u on the ventral side because the concave portion 19u can further fit to the shape of the gluteal region.

The concave portions 17u and 19u are under the force of closing due to the deformation when the diaper is worn. To allow the concave portions 17u and 19u to be functional in a more reliable manner, it is preferable to provide concave portion deformation elastic members 30 that exert contraction force in a direction that brings the width-direction both side edges of the concave portions 17u and 19u closer to each other. Providing these concave portion deformation elastic members 30 makes it possible to facilitate the deformation of the concave portions 17u and 19u in such a manner as to close and keep elastically the concave portions 17u and 19u in the closed state. The concave portion deformation elastic members 30 may be omitted.

The outer body 20 of the underpants-type disposable diaper as in the illustrated mode is generally provided with the elastic members 25, 26, and 28 ranging from one side seal portion 21 to the outer side seal portion 21 to improve a fit. Some of the elastic members 25, 26, and 28 are arranged as the concave portion deformation elastic members 30 crossing over the concave portions 17u and 19u. Alternatively, dedicated elastic members may be separately attached as the concave portion deformation elastic members 30. Although the curved elastic members 26 and 28 are used in the illustrated mode, the waist lower portion elastic members 25 may be used instead.

Figure 13:
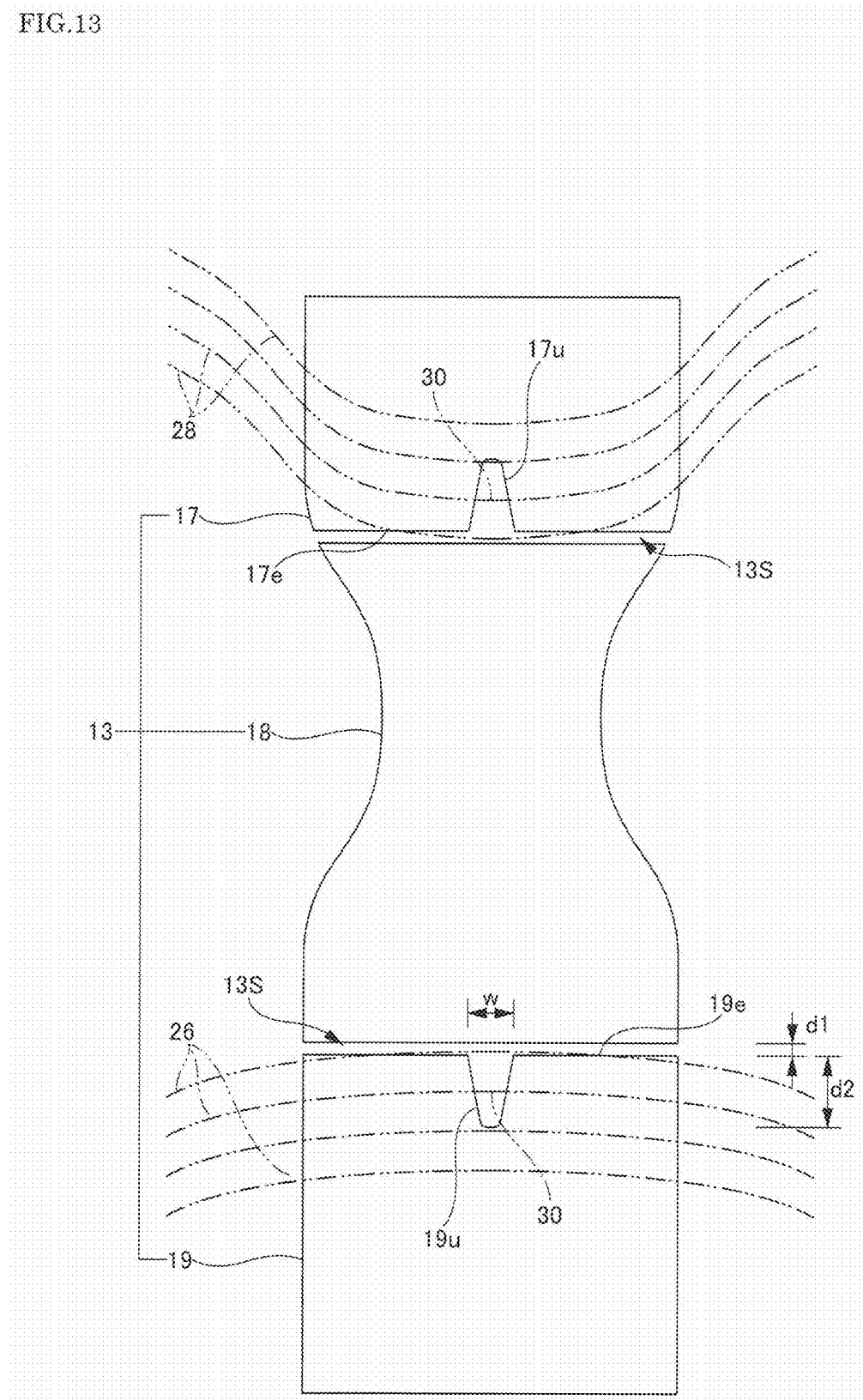
FIG. 13 is a plane view of major components of the absorber.

The concave portion deformation elastic members 30 may be arranged linearly along the width direction in such a manner as to cross over the concave portions 17u and 19u. Alternatively, the concave portion deformation elastic members 30 may be arranged in such a manner as to curve toward the crotch portion and cross over the concave portions 17u and 19u as illustrated in FIG. 13 so that the concave portion deformation elastic members 30 can be more effective in facilitating the deformation of the concave portions 17u and 19u in such a manner as to close and keeping elastically the concave portions 17u and 19u in the closed state. In particular, this arrangement of the concave portion deformation elastic members 30 is suitable for the case where the concave portions 17u and 19u are smaller in width with increasing proximity to the waist side as in the illustrated mode. To arrange the concave portion deformation elastic members 30 in a curved pattern, the curved elastic members 26 and 28 are preferably used as in the illustrated mode.

In the case of providing the fit elastic members 25, 26, and 28 to the outer body 20 of the underpants-type disposable diaper, it is preferable to cut finely at least width-direction intermediate portions of the fit elastic members 25, 26, and 28 in the region of the outer body 20 overlapping the inner body 10 to prevent unnecessary contraction of the inner body 10 as described above. However, cutting the portions of the fit elastic members 25, 26, and 28 overlapping the concave portions 17u and 19u makes it impossible to form the concave portion deformation elastic members 30. Accordingly, as illustrated in FIG. 8, it is preferable to cut finely the fit elastic members 25, 26, and 28 in the cutting pattern CP excluding the portions that constitute the concave portion deformation elastic members 30.

The crotch portion of the absorber 13 may be provided with a concave portion such as a slit or an embossed portion for the purpose of improving a fit, liquid diffusibility, and the like. For example, as illustrated in FIG. 14, a vertical slit 18S (or embossing) ranging from the ventral-side concave portion 17u to the dorsal-side concave portion 19u may be formed in the width-direction center of the crotch absorber 18 and set as an easily folded portion extending in the front-back direction. Providing the easily folded portion to the conventional absorber 13 would cause the deformation of the absorber 13 resulting from the easily folded portion to exert influence on the ventral-side portion and the dorsal-side portion. In the illustrated mode, however, the width-direction slits 13S reduce the influence.

INDUSTRIAL APPLICABILITY

The present invention is applicable to all general disposable diapers including, tape-type disposable diapers, and pad-type disposable diapers as well as the underpants-type disposable diapers as in the example described above.

REFERENCE SIGNS LIST

B Back panel
F Front panel
d1 Interval width
d2 Depth
10 Inner body
11 Liquid pervious face sheet
12 Liquid impervious back sheet
13 Absorber
13N Narrower part
13S Width-direction slit
14 Package sheet
15 Gather nonwoven fabric
16 Gather elastic member
17 Vertical-side absorber
17e Back edge
17u and 19u Concave portion
18 Crotch absorber
18S Vertical slit 19 Dorsal-side absorber
19e Front edge
20 Outer body
20C Folded portion
21 Side seal portion
24 Waist portion elastic member
25 Waist lower portion elastic member
26 and 28 Curved elastic member
26 Dorsal-side curved elastic member
28 Ventral-side curved elastic member
29 Leg line
30 Concave portion deformation elastic member

The invention claimed is:

1. A disposable diaper comprising:
a crotch portion;
a ventral-side portion extending toward the ventral side of the crotch portion;
a dorsal-side portion extending toward the dorsal side of the crotch portion;
an absorber in the crotch portion, the ventral-side portion, and the dorsal-side portion, and
a concave portion having no absorber and formed at a width-direction center of a width-direction slit,
wherein the absorber is divided in a front-back direction by the width-direction slit entirely extending in the width direction from left side edge to right side edge of the absorber and provided on at least one of front and back sides of the crotch portion, wherein the absorber in the crotch portion is in a same plane as the absorber in the ventral-side portion and the absorber in the dorsal-side portion, and
wherein the concave portion extends from a waist side edge of the with-direction slit and recesses toward a waist side of the disposable diaper, wherein width-direction both side edges of the concave portion are deformed to close the concave portion so that a portion of the absorber surrounding the concave portion is rounded along a surface of a wearer's body.

2. The disposable diaper according to claim 1, wherein the concave portion is shaped in such a manner as to be narrower with increasing proximity to the waist side.

3. The disposable diaper according to claim 1, comprising concave portion deformation elastic members that exert a contraction force in the width-direction to bring both side edges of the concave portion closer to each other.

4. The disposable diaper according to claim 3, wherein the concave portion deformation elastic members are elongated elastic members that are arranged in such a manner as to curve toward the crotch portion and cross over the concave portion.

5. The disposable diaper according to claim 3, comprising:
an outer body constituting individually or integrally a front panel and a back panel; and
an inner body that includes the absorber and is attached on an inner side of the outer body ranging from the front panel to the back panel, the outer body of the front panel and the outer body of the back panel being joined together at both side edges to form side seal portions, thereby forming a waist opening and a pair of right and left leg openings, wherein
fit elastic members are provided in the outer body from one side seal portion to the other side seal portion, and
a portion of the fit elastic members are arranged as the concave portion deformation elastic members in such a manner as to cross over the concave portion.

6. The disposable diaper according to claim 5, wherein the fit elastic members at least in a width-direction intermediate portion overlapping the inner body are cut between side edges of the crotch portion and the concave portion to make the fit elastic members being cut non-contractible and to keep the concave portion deformation elastic members being contractible.

7. The disposable diaper according to claim 1, wherein at least one of the width-direction slits is formed in such a manner that a clearance width becomes larger with increasing proximity to width-direction both sides.

8. The disposable diaper according to claim 1, wherein an easily folded portion extending in a front-back direction is formed in a width-direction center of the absorber.

* * * * *